United States Patent [19]

Leschonski et al.

[11] Patent Number: 4,718,288
[45] Date of Patent: Jan. 12, 1988

[54] METHOD AND AN APPARATUS FOR SPLITTING SAMPLES OF POWDERS AND SUSPENSIONS

[76] Inventors: Kurt Leschonski, Am Dammgraben 20; Stephan Röthele, Am Rollberg 5, both of 3392 Clausthal-Zellerfeld, Fed. Rep. of Germany

[21] Appl. No.: 729,055

[22] Filed: Apr. 30, 1985

[30] Foreign Application Priority Data

May 4, 1984 [DE] Fed. Rep. of Germany ....... 3416595

[51] Int. Cl.[4] .......................... G01N 1/18; G01N 1/20
[52] U.S. Cl. .................................. 73/863; 73/863.31; 73/863.45; 73/863.52; 73/863.58; 141/34
[58] Field of Search ................ 73/863, 863.31, 863.41, 73/863.43, 863.45, 863.51, 863.52, 863.56, 863.57, 863.58, 863.61; 366/140; 141/34

[56] References Cited

U.S. PATENT DOCUMENTS

| | | | |
|---|---|---|---|
| 457,145 | 8/1891 | Bridgman | 73/863.56 |
| 797,144 | 8/1905 | Nickerson | 73/863.45 X |
| 1,020,251 | 3/1912 | Behr et al. | 73/863.51 X |
| 1,970,597 | 8/1934 | Cotton | 366/140 |
| 2,848,144 | 8/1958 | Haskell et al. | 73/863.45 X |
| 3,716,167 | 2/1973 | Huntington | 73/863.45 |
| 3,747,622 | 7/1973 | Reinhall | 73/863.45 |
| 4,126,043 | 11/1978 | Schurmann | 73/863.51 X |

FOREIGN PATENT DOCUMENTS

| | | | |
|---|---|---|---|
| 2164672 | 8/1973 | Fed. Rep. of Germany ... | 73/863.45 |
| 411307 | 6/1910 | France | 73/863.45 |

Primary Examiner—Tom Noland
Attorney, Agent, or Firm—Kenyon & Kenyon

[57] ABSTRACT

A method for splitting samples of particulate matter (powders or suspensions), by which a powder or suspension stream of a sample is subdivided several times into subsamples and an analysis sample obtained therefrom, involves forming a powder or suspension stream rotating it centrifugally throwing off the stream and dividing it up several times into subsamples in the tangential throw-off direction and collecting divided subsamples, whereby one or more subsamples may be recycled into the stream of particles. An apparatus for carrying out this method (a sample splitter) comprises a central pipe which is capable of being rotatably driven, to which the powder or suspension is fed in batches, and which has a curved lower discharge end. In the throw-off area of the stream of particles centrifuged by this central pipe, a stationary ring of pockets is arranged for forming subsamples, these pockets being separated from each other by several, up to n=32, sharp-edged webs equally spaced in circumferential intervals and facing the stream of particles. Due to the displacement of the material away from the rotational axis of the central pipe, which increases towards the discharge end, a centrifugal effect is created which leads to an acceleration of the movement of the stream of particles to be split, thereby thinning or reducing the cross sectional area of the powder or suspension stream and promoting the separation of the particles.

14 Claims, 14 Drawing Figures

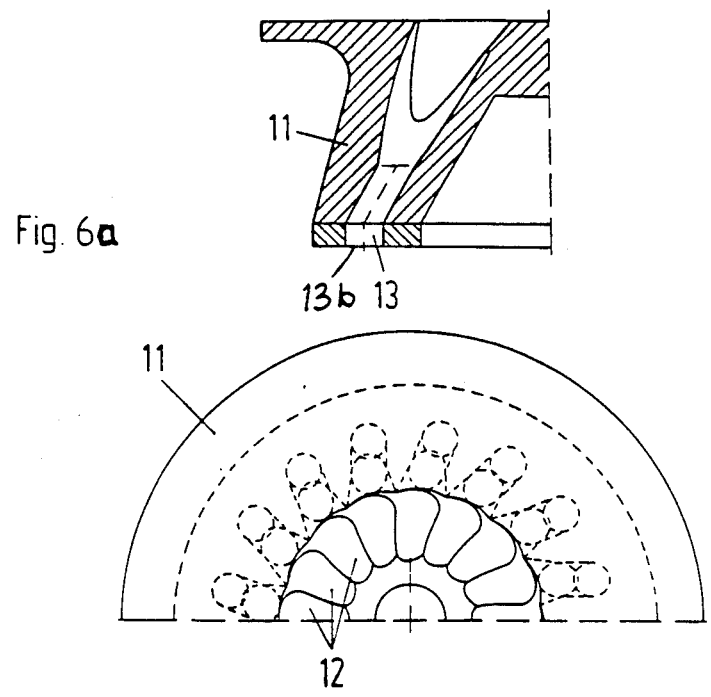
Fig. 6a
Fig. 6
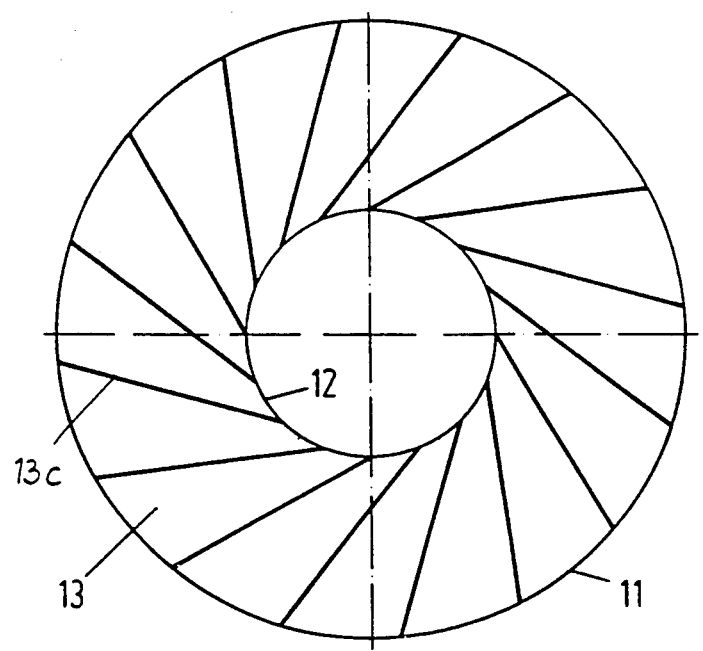
Fig. 7

METHOD AND AN APPARATUS FOR SPLITTING SAMPLES OF POWDERS AND SUSPENSIONS

BACKGROUND OF THE INVENTION

The present invention relates to a method and an apparatus for splitting samples of particulate matter, which may be applied both to dry powders and to particles which are suspended in liquids.

Methods and apparatus for splitting samples are used both in production and in laboratories when representative samples have to be prepared for assessing the quality of large product quantities of particulate matter. The manual methods of sample splitting include collecting samples of large product quantities (trucks, shiploads, railway wagons) and splitting them into analysis samples by coning and quartering, which is used for feed material quantities of up to approximately 1 $m^3$.

Static sample splitters are used when smaller feed material quantities of up to approximately 0.1 $m^3$ are to be reduced into analysis samples. However, for the purposes of measurement in a laboratory, final sample amounts or quantities of only a few grams (e.g. for screen analysis) down to a few milligrams (for sedimentation analysis) and even less than 1 mg (for counting methods) are generally required. Therefore, in the case of both large and medium-sized initial or sampling quantities, the efforts involved in sample splitting increase and the quality of the sample splitting must become more reliable as the reduction to smaller analysis samples via subsamples increases. For reasons of statistical certainty when obtaining and ensuring the representative composition of the reduced subsamples, each of these subsamples must be composed of as many even smaller subsamples as possible during the splitting of the samples. The manual effort involved and other reasons restrict the reliable applicability of static chute splitters for the purpose.

Spinning chute splitters bring about much more reliable sample splitting results because only very small final systematic errors must be expected as the initial amount of material is subdivided into thousands of subsamples (14,400 subsamples of approximately 35 mg may be obtained by a riffler splitter which divides the incoming stream of particles into eight subsamples, when in 15 minutes 500 g are fed to the riffler spinning at 120 rpm). Extremely small representative analysis samples can be taken only from pastes or suspensions because only then a subsample may be taken as a random sample from the homogenously mixed material. Pastes are indispensable when large particles would be deposited as sediment in suspensions.

Therefore, it is an object of the invention to provide a novel and useful method and apparatus for sample splitting to obtain extremely small analysis samples from large amounts of feed material with extremely low systematic or statistical errors without having to apply sample splitting in pastes when the sample contains coarse particles.

SUMMARY OF THE INVENTION

The method for splitting samples of particulate matter (powders or suspensions) according to the invention, comprises the steps of forming a powder or suspension stream from the sample, rotating said stream of particles, subdividing said rotating stream of particles into several subsamples, collecting said subsamples in the direction of the trajectories of the particles, combining some of the subsamples and repeating the steps of rotating, subdividing and collecting until one or several combined subsamples form an analysis sample.

An embodiment of this method involves recycling one or more subsamples into the stream of particles.

An apparatus for carrying out this method has in accordance with the invention a central pipe which is at least approximately vertical, to which the stream of particles is fed in batches and which is rotatable and has a curved lower discharge end, as well as a stationary ring of pockets for forming subsamples in the throw-off area of the stream of particles thrown of centrifugally by said central pipe, the pockets being separated from each other by sharp-edged webs which face the stream of particles and are arranged at equal peripheral intervals. The pockets are open-ended channels.

The claimed method modifies the described principle of the spinning chute splitter insofar as it is no longer the case that the feed quantities rotate and the stream of particulate material moving under the effect of gravity is divided up via a static splitter head, but instead the spinning is shifted to batches of a vertical powder or suspension stream. The stream of material to be split, which initially extends vertically, is then deflected by up to approximately 90°. The displacement of the movement of the material away from the center of rotation, which increases towards the discharge, gives rise to a centrifugal effect leading to an acceleration of the stream of material, thereby reducing the cross sectional area of the powder or suspension stream.

Following the trajectory direction, the powder or suspension stream dissolves into a thin stream, which is divided up into a plurality of subsamples—preferably up to 32—per revolution by a stationary ring of pockets immediately behind the plane of rotation.

In a preferred embodiment, the flanks of the sharp-edged webs are formed as inclined side walls or surfaces which follow the trajectories of the particles thrown off the rotor and laterally limit the pockets inclined at an angle of 30° to 60°, as well as curved or inclined pocket covers for guiding the stream of particles, and curved or inclined bottoms such that no deposits obstruct the free flow of the stream of powder or suspension. The side walls limiting the individual pockets begin at the sharp edges of the webs and are oriented approximately parallel to the direction of flight of the individual particles, so that the side walls are inclined at an angle of 30° to 60° with respect to the radial direction. This prevents adhesion and abrasion, which would have an unfavorable effect on the splitting, process, due to the impingement of the powder or suspension stream on the wall.

The inclination of the side walls brings about the vertical arrangement of the webs on the ring of pockets in order to guarantee sharp edges of the webs and thus clear sample splitting conditions. If the sharp edges of the webs are not, or not entirely, vertical, thereby resulting in entrance openings in the ring of pockets which are, for example, trapezoidal when regarded from above, clear sample splitting conditions with respect to the uniformity of the subsample are only obtained when the rotational axis of the powder or suspension stream coincides with the center axis of the ring of pockets and the thrown-off stream of particles is dynamically balanced.

Preferably, pocket covers are provided which are curved by 90° or correspondingly inclined so that the stream of particles is carefully guided into subsample vessels, e.g. receiving jars. which are hung in position vertically on the outer periphery on the bottom side. At the same time, pocket bottoms may be designed in such a way that no deposits can obstruct the free flow of the stream of particles. These design measures are preferably realized in a central splitter core. In this splitter core, an entrance opening for each subsample, which is preferably trapezoidal and vertical on the inner radius, is formed in the manufacturing process into a discharge opening for the subsample, which is horizontal on its lower side. The axis of the resulting conduit connecting the openings extends in the throw-off direction of the stream of particles, i.e. is inclined with respect to the radial direction. This results in four preferred embodiments.

In the first of these, the conduits are bored in the direction of flight from the outside towards the inside and from the bottom towards the top towards the ring of pockets, or correspondingly from the inside towards the outside and from the top towards the bottom. The circular discharge openings for connection with the subsample vessels are preferably counterbored, while the vertical flanks of the webs may be milled to form the ring of pockets.

In the second and third embodiments, the central splitter core has a divided design, the conduits being formed either in the top portion, for example by a plain milling cutter, whereby the conical bottom portion ensures that the bottom end is inclined; or else in the bottom portion, for example by an end-milling cutter, a turned-out top portion conforming to the trajectory parabolically being provided as a pocket cover. Here, too, the discharge openings for the subsample vessels are provided by overreaching counterbores in the bottom portion.

In the fourth embodiment, the conduits are bored as in the first embodiment, but the ring of pockets is worked into the undivided splitter core by circulating beveled cuttings, the cone point and circulatory axis of which are located on the particular center axis of the conduit.

The splitter core is placed in the center of a glass container or pipe which is preferably available commercially and is located in a C-shaped housing open towards the front. In the base of the housing, there are not only operating and switching elements drawn out towards the front, but also a base plate for a collecting vessel made of glass, this base plate being adjustable from the side via an eccentric or lever. In a back wall of the housing which connects a base stably to a housing head, driving elements for the rotatable central pipe are provided. The central pipe is located in the prolonged axis of the glass container and the splitter core, and is driven via a belt drive. The material is fed from a stationary hopper which is placed on the housing lid (head), the feed sample being capable of being provided in batches of a powder or suspension stream from supply vessels with commercially available vibrating conveyers.

The lower curved discharge end of the central pipe capable of being rotatably driven (its inside diameter being about 16 mm, for example) protrudes into the splitter core to an extent that the radially thrown-off powder or suspension stream reaches the entrance openings of the pockets arranged directly opposite of the central pipe. The distance between the end of the central pipe and the stationary flanks of the webs of the ring of pockets may be up to 5 mm, or up to 10 mm in special cases. This ensures that coarse powders can be split without blocking or choking the system.

The number of subsamples collected may optionally be determined by placing the splitter core on the collecting vessel. From all pocket openings, on whose conduit ends no subsample vessels are placed, subsamples are collected and mingled together in one collecting vessel or receptable. This makes it possible to collect, as an analysis sample, either one representative subsample or all representative subsamples from the overall subdivided sample. The subsamples are removed together with the splitter core after lowering the self-centering collecting vessel. The collecting vessel is—in operation—pressed sealingly against a head portion of the housing by aid of the adjustable base plate. The lowering movement releases the seal, lowering the upper edge of the splitter core to a level at which the collecting vessel with the insert can be drawn past unobstructed below the discharge end of the central pipe.

After the subsample vessels have been replaced, the device can be prepared and used for the next splitting process.

Special designs may be such that the entire drive and operating portion is placed on the collecting vessel and the splitter core so that the surrounding housing can be dispensed with. The samples are then removed in the manner described after the driving unit which is placed on has been removed.

Special designs of the splitter core may be such that a reduction of the requirements set on the sample splitting is accompanied by a reduction of the efforts involved in manufacturing the conduits along with the entrance and exit geometry. Thus, one can conceive of splitter cores which are equipped with only 16, 8, 4, 2 or only one ring of pockets, conduit and collecting vessel according to the same principle for producing a small number of subsamples.

Embodiments of the invention shall be described in more detail with reference to a schematic drawing. The figures show:

BRIEF DESCRIPTION OF THE DRAWINGS

FIGS. 1 and 1a two vertical sections 1a—1a and 1—1, respectively, rotated by 90° from each other, of a sample splitter having a C-shaped housing, FIG. 2 the splitter head of a sample splitter as in FIG. 1, in an enlarged view, FIG. 3 a subsample vessel hung on the stationary splitter core of the splitter head as in FIG. 2, FIG. 3a a section along line 3a—3a of FIG. 3, FIGS. 4 and 4a a top view and a sectional view of a first embodiment of a stationary bipartite splitter core for a sample splitter according to the invention, FIGS. 5 and 5a a top view and a sectional view of a second embodiment of a stationary bipartite splitter core for a sample splitter according to the invention, FIGS. 6 and 6a a top view and a sectional view of a stationary one-part splitter core for a sample splitter according to the invention, FIG. 7 a top view of a stationary splitter core made of thin-walled web plates or sheet metal plates for a sample splitter according to the invention, FIG. 8 a form modified with respect to FIG. 1 of the upper portion of a housing of the sample splitter, FIG. 9 a schematic view of the connection of a sample splitter to a conveying pipe for a suspension from which an analysis sample is to be obtained.

DETAILED DESCRIPTION

Figure 1:
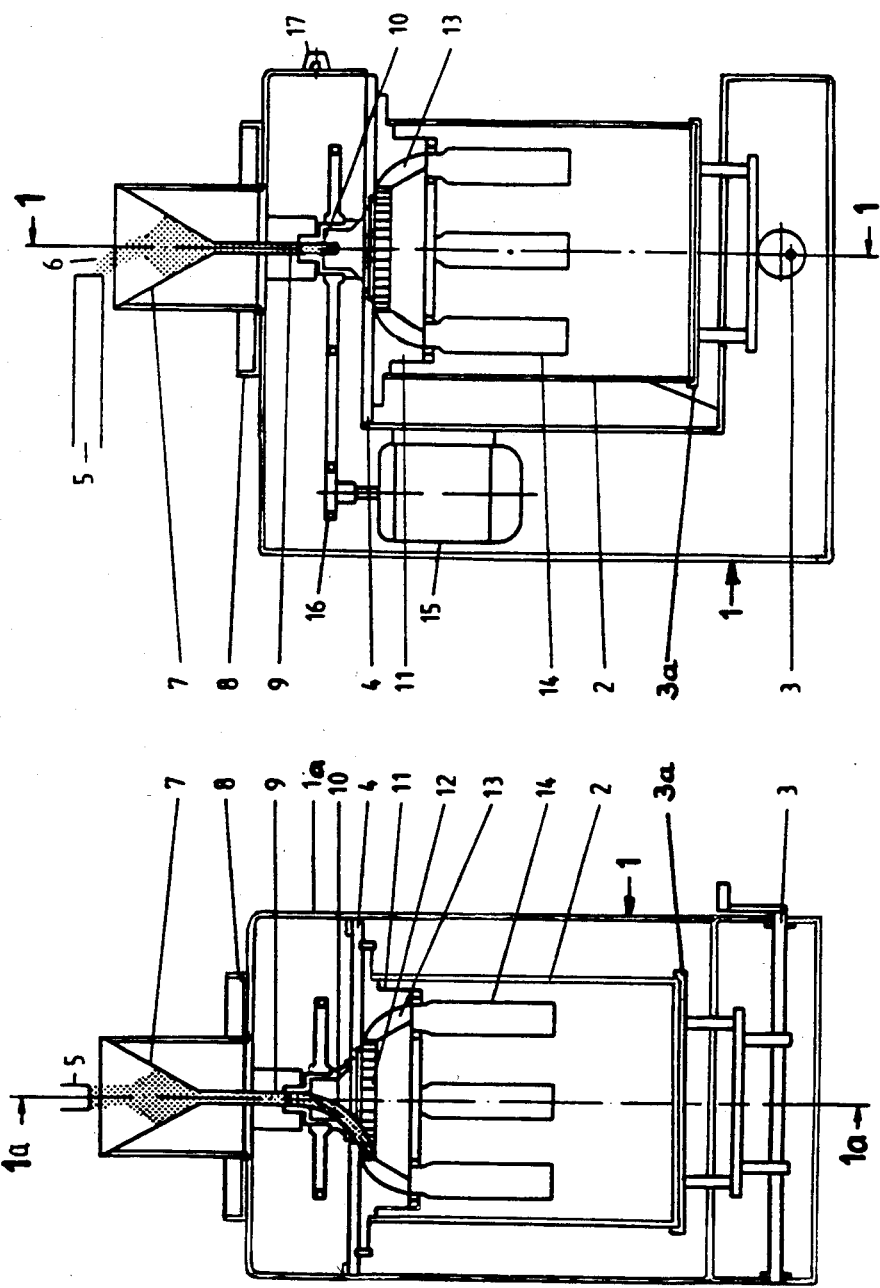

FIGS. 1 and 1a show, in two vertical sections 1a—1a and 1—1 respectively, rotated by 90° from each other, the construction of inventive sample splitter in accordance with the invention having a C-shaped housing 1. A collecting vessel 2 is placed in housing 1 on a base plate 3a and pressed against head plate 4 in a sealing manner and a centered position via an eccentric elevating mechanism 3. A sample 6 in the form of a powder stream, which is to be divided into analysis samples, is fed into a feed hopper 7 from a commercially available feeding channel 5 for particulate material or from corresponding auxiliary means for suspensions. A concentric overflow vessel 8 collects incorrectly fed excess quantities. Sample 6 enters, via a stationary discharge pipe 9, a central pipe 10 which is capable of being rotatably driven and is formed into the shape of a quarter circle. Central pipe 10 rotates the stream of particles and discharges it at its free discharge end from where it reaches in free flight along trajectories through a gap a splitter core 11.

The freely flying stream of particles is taken up in the peripheral direction by a concentric ring 12 of pockets subdivided or chopped up into subsamples and is fed via conduits 13 to a corresponding number of subsample vessels 14 or collected again in collecting vessel 2. In the crosspiece of the C-shaped housing 1 there is a driving motor 15 provided which sets central pipe 10 rotating, for example via a belt drive 16. Electrical switching elements 17 are disposed at one front wall of a top portion 1a of the housing 1.

Figure 2:
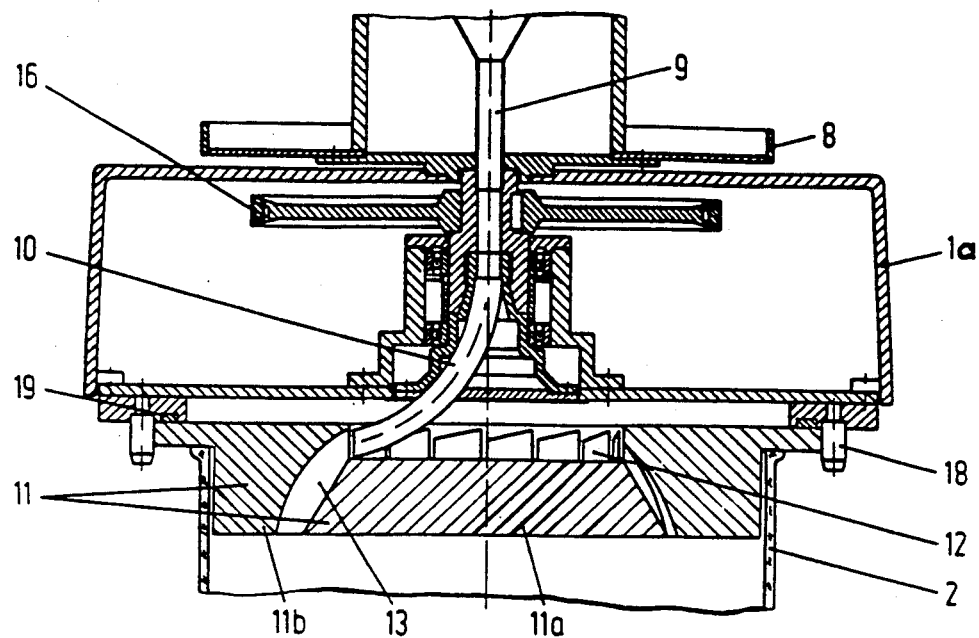

FIG. 2 shows a top portion 1a of housing 1 and splitter core 11 in detail in cross-section. Stationary discharge pipe 9 ends in a driven bearing position of central pipe 10. Central pipe 10 ends directly before ring 12 of pockets. Openings in ring 12 of pockets form areas for the stream of particles to enter conduits 13 which guide the substreams. Splitter core 11 shown here consists of a conical bottom portion 11a and a top portion 11b, into which the conduits are worked using a plain milling cutter. Top portion 11b is centered with its outer periphery on housing pins 18 and sealed off by a radial ring 19 when splitter core 11 is inside collecting vessel 2 in its upwardly pressed position.

Figure 3:
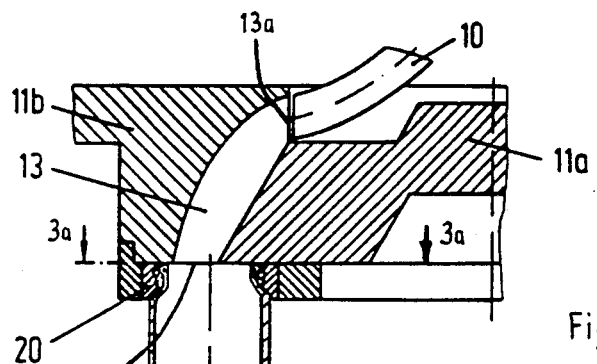
Figure 3A:
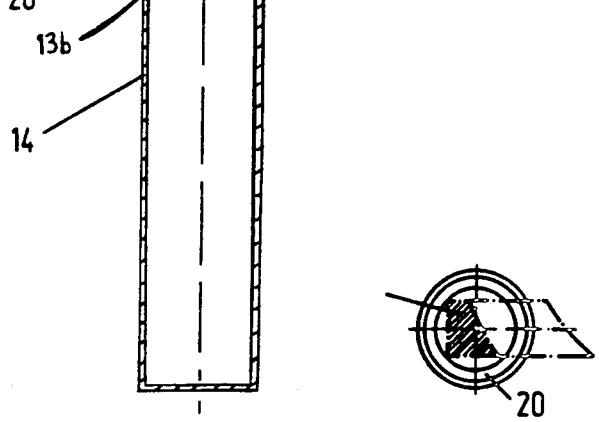

FIG. 3 shows a subsample vessel 14 hung by a snap-on means 20 on discharge opening 13b of conduits 13. FIG. 3a shows, in section 3a—3a, the position and shape of discharge opening 13b in the overreaching neck opening of subsample vessel 14. Commercially available sample jars can thus be simply mounted and dismounted, and stored separately in a sealed state.

Figure 4:
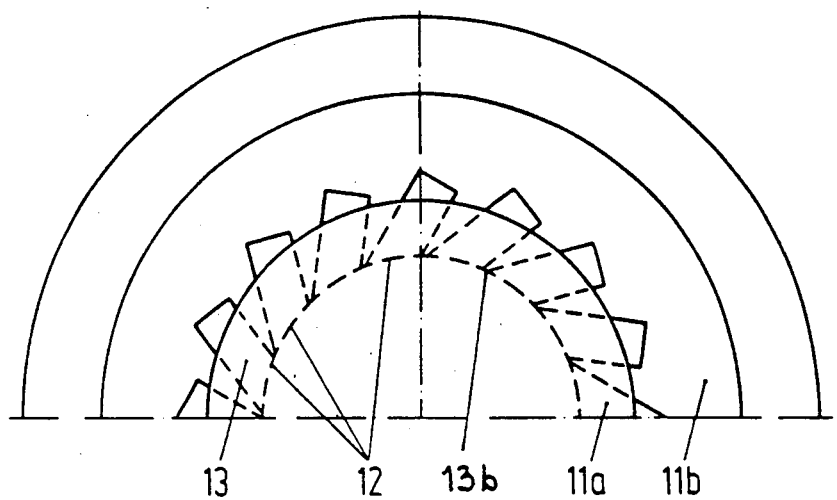
Figure 4A:
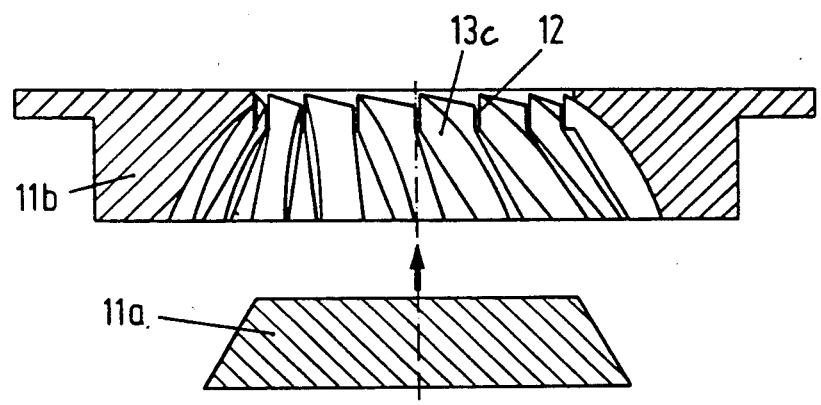

In FIGS. 4 and 4a a first embodiment of splitter core 11 is depicted. FIG. 4 shows half the top view of the underside of splitter core 11, which may be seen in FIG. 4a in cross-section in an exploded view showing the top and bottom portions. Conduits 13 are worked into top portion 11b in the throw-off direction by a plain milling cutter in such a way as to produce webs 13c on the inside radius of ring 12 of pockets which are as sharp-edged as possible and are vertical, and so that the limiting outside surfaces of conduits 13 guide the stream of particles in the shape of a quarter circle to the lower horizontal discharge area of splitter core 11. The conical inside surface of conduits 3 is formed by the conical outside surface of bottom portion 11a which is centered in the top portion 11b.

Figure 5A:
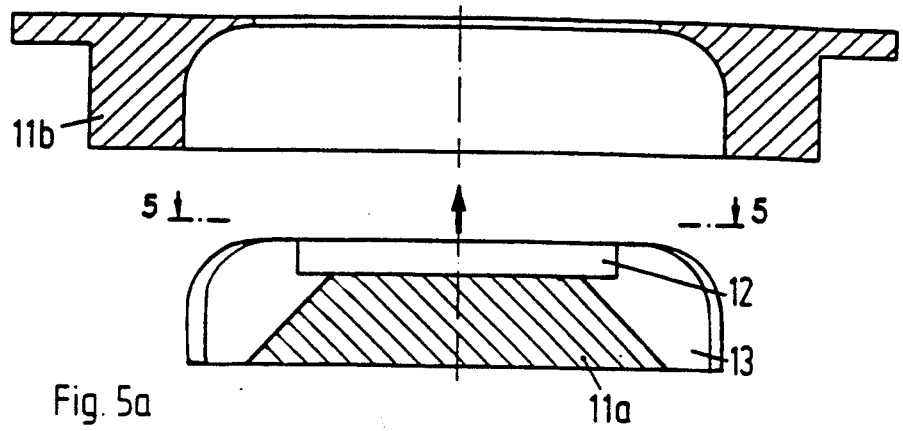
Figure 5:
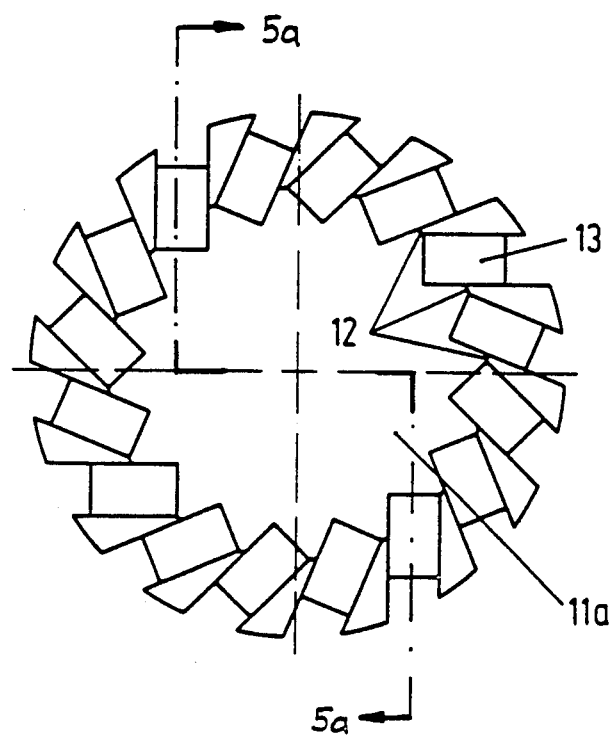

In FIG. 5, the bipartite splitter core 11 is designed, in a second embodiment, in such a way that conduits 13 are produced in bottom portion 11a by an end-milling cutter and the outer covers of the conduits 13 are formed by top portion 11b which is turned out accordingly. The more simple milling work is counteracted by more difficult centering. However, sharp-edged webs 13c of ring 12 of pockets may be obtained more easily. Furthermore, slide-down surfaces of conduits 13 undercut the entrance openings 13a on ring 12 of pockets so that extremely small deposit surfaces remain for faulty splitting when the particles are fed from the central pipe 10. FIG. 5 shows the top view 5—5 of the milling surface of the bottom portion 11a, while FIG. 5a shows bottom portion 11a and top portion 11b in an exploded, sectional view.

FIGS. 6 and 6a show splitter core 11 made of one piece, from the top and in an axial section, respectively. Ring 12 of pockets and conduits 13 come about when the conduits are bored in the lower discharge portion and are produced in the upper entrance portion by circulating beveled cuttings. This gives rise to sharp edges of the webs 13c, which have the shape of a hysteresis curve when seen from the top and appear as parabolic funnels open at the top when seen in cross-section. The exact geometrical contour results from the intersection of a cylinder in alignment parallel to the axis with the envelope of a cone, and nesting them into each other in a cascade-like manner at one outer periphery, the distance between the axes of symmetry necessarily being smaller than the diameter of the limiting beveled cutter so that there is also intersection between the envelopes of the cones. These intersection lines form ring 12 of pockets.

FIG. 7 shows the design of splitter core 11, conduits 13 and ring 12 of pockets made of thin-walled web plates, as a further possibility.

Figure 8:
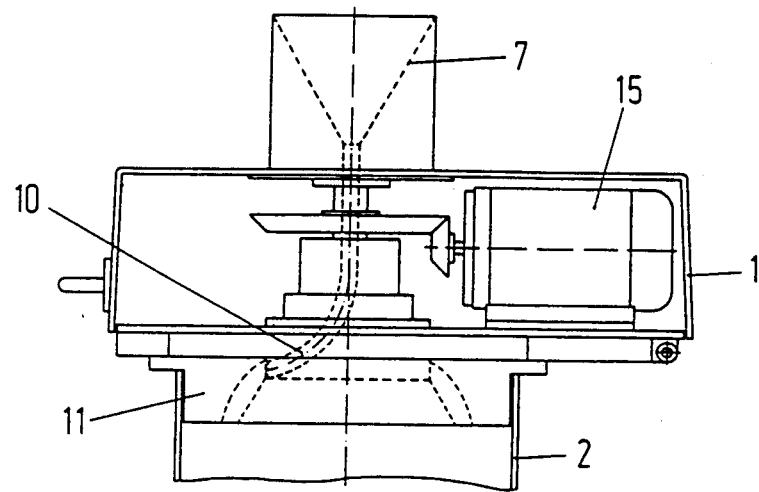

In FIG. 8 the construction of the housing of FIG. 1 is developed into one in which only the top portion of the C-shaped housing is retained. Driving motor 15 and central pipe 10 are assembled together with hingedly mounted feed hopper 7 in a housing 1 and are placed on a collecting vessel 2 together with splitter core 11. This design is particularly well-suited for inserting the sample splitter into an on-line process measuring arrangement.

Figure 9:
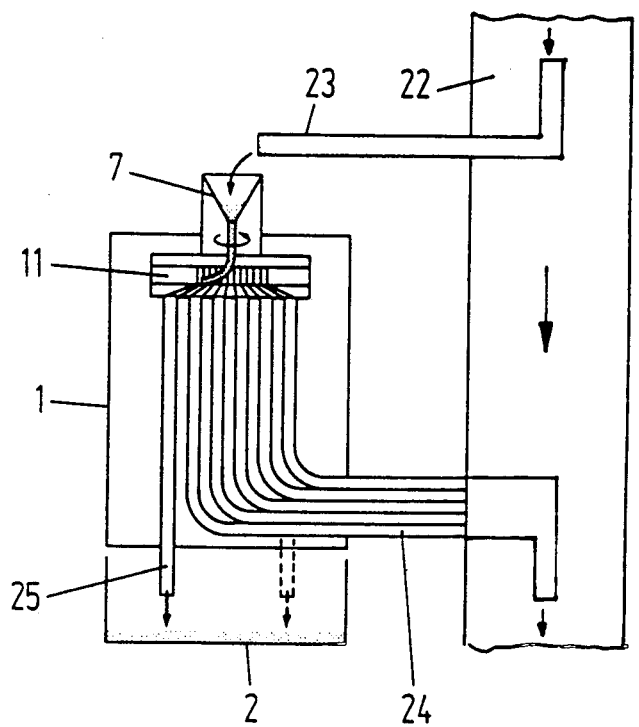

Finally, FIG. 9 shows the incorporation of the sample splitter into an on-line sample splitting process. A suspension feed sample stream 23 taken representatively from a multiphase conveyor pipe 12 is fed into feed hopper 7 of the sample splitter, by the central pipe which is curved outwardly towards the discharge, rotated and divided up into a plurality of subsamples in splitter core 11. After sample splitting, selected subsample streams 25 are collected as an analysis sample in collecting vessel 2, and the remaining subsample streams 24 combined and recycled into conveyor pipe 22.

We claim:

1. A method for splitting samples of particulate matter, comprising the steps of:
    (a) forming a stream of particles of the same form as the selected sample from the selected sample;
    (b) imparting a rotational velocity and axially outwardly directed trajectory to said stream of particles to form a rotating axially outwardly directed stream of particles;

(c) subdividing said rotating stream of particles into several subsamples of equal angular increments;

(d) collecting said subsamples in the direction of the trajectories of the particles; and (e) combining some of the subsamples and repeating the steps of imparting, subdividing and collecting to obtain at least one subsample for use as an analysis sample.

2. The method according to claim 1, wherein at least one subsample is recycled into the stream of particles.

3. An apparatus for splitting samples of particulate matter by splitting samples of a stream of particles of the same form as the selected sample from a selected sample several times into subsamples from which an analysis sample is obtained, comprising:

(a) a central pipe which is at least approximately vertical at an upper end, to which upper end the stream of particles is fed in batches and which pipe is capable of being rotatably driven and has a curved lower discharge end;

(b) a stationary ring of open-ended pockets for forming subsamples in a throw-off area of the stream of the stream of particles thown off centrifugally by said central pipe as it is rotatably driven, the particles in the stream of particles having trajectories fixed immediately upon the throwing off of the particles by said central pipe, said pockets being separated from each other by sharp-edged webs which face the stream of particles and are arranged at equal angular intervals, said sharp-edged webs having generally vertically oriented side walls which follow said trajectories and laterally limit the pockets, said walls being inclined at an angle of 30° to 60° with respect to radii of the apparatus.

4. The apparatus according to claim 3, wherein said pockets further include curved or inclined pocket covers for guiding the stream of particles and curved or inclined bottoms such that no deposits obstruct the free flow of the stream of particles.

5. The apparatus according to claim 4, wherein each pocket has an entrance opening in a vertical plane of rectangular cross-section, running into a horizontal discharge opening, that is, the cross-section thereof is disposed in a horizontal plane, on which standardized subsample vessels, comprising sample jars with snap-on caps, may be provided along the entire periphery in such a way that their openings completely cover the horizontal discharge openings.

6. The apparatus according to claim 5, wherein each entrance opening is connected to the corresponding horizontal discharge openings by a conduit, which is formed in a splitter core having a bottom portion and inclined with respect to a radius of the splitter core at an angle which corresponds to the throw-off direction of the stream of particles.

7. The apparatus according to claim 6, wherein the conduits are bored into the bottom portion of the splitter core in the direction of flight of the stream of particles, the flanks of the webs are milled at the top by circulating milling and horizontal discharge openings for the subsample vessels are provided on the bottom.

8. The apparatus according to claim 6, wherein the splitter core comprises a conical bottom portion and a top portion, the conduits are worked into the top portion using a plain milling cutter and covered by the bottom portion, and horizontal discharge openings for the subsample vessels are provided at the bottom.

9. The apparatus according to claim 6, wherein the trajectory of said stream of particles is parabolic and the splitter core comprises a bottom portion and a turned-out top portion conforming with the trajectory parabola of the stream of particles, the conduits are worked into the bottom portion using an end-milling cutter, covered by the top portion and horizontal discharge openings for the subsample vessels are provided at the bottom.

10. The apparatus according to claim 6, wherein the splitter core is made up of thin-walled web plates.

11. The apparatus according to claim 6, wherein the splitter core is coaxially placed on a collecting vessel which is supported by a vertically adjustable base plate in a housing below the central pipe, said central pipe being disposed in a head portion of the housing, said splitter core being capable of being sealingly pressed against said head portion and lowered from said head portion to a level such that the collecting vessel together with the splitter core may be drawn past below the discharge end of the central pipe and removed from the housing.

12. The apparatus according to claim 6, wherein the splitter core is designed to be placed on a collecting vessel and the central pipe together with a driving, operating and feed sample feeding unit is designed to be placed on the splitter core in a centered position.

13. The apparatus according to claim 3, wherein a feed hopper is arranged in a stationary position on the housing above the central pipe.

14. The apparatus according to claim 3, wherein the ring of open-ended pockets includes up to 32 pockets.

* * * * *